United States Patent [19]
Ogata et al.

[11] Patent Number: 5,599,807
[45] Date of Patent: Feb. 4, 1997

[54] STEROID DERIVATIVES

[75] Inventors: Kazumi Ogata, Toyonaka; Takahiro Sakaue, Itami; Yuuichi Isowaki, Settsu; Hidetoshi Nakao, Itami; Kazuhiko Ito, Amagasaki, all of Japan

[73] Assignee: Senju Pharmaceutical Co., Ltd., Osaka, Japan

[21] Appl. No.: 356,962

[22] Filed: Dec. 16, 1994

[30] Foreign Application Priority Data

Dec. 22, 1993 [JP] Japan ................... 5-324405

[51] Int. Cl.⁶ .................. C07J 43/00; A61K 31/58
[52] U.S. Cl. ................... 514/176; 540/110
[58] Field of Search ................... 540/107, 113, 540/110; 514/176

[56] References Cited

U.S. PATENT DOCUMENTS

| | | | |
|---|---|---|---|
| 4,181,669 | 1/1980 | Hansen et al. | 260/397.4 |
| 5,380,839 | 11/1995 | McCall et al. | 540/107 |

FOREIGN PATENT DOCUMENTS

| | | |
|---|---|---|
| 2300570 | 9/1976 | France . |
| 421957 | 4/1967 | Switzerland . |
| WO90/01933 | 3/1990 | WIPO . |

OTHER PUBLICATIONS

Nakagome et al., Chemical Abstracts, vol. 82, No. 21 26 May, 1975 Columbus, Ohio U.S. Abstract No. 140109K.

*Primary Examiner*—Mukund J. Shah
*Assistant Examiner*—Anthony Bottino
*Attorney, Agent, or Firm*—Wenderoth, Lind & Ponack

[57] ABSTRACT

This invention provides a novel steroid derivative having the structure of an ester between the carboxyl group of a quinolonecarboxylic acid and the alcoholic hydroxyl group in 21-position of asteroid compound, which has the following formula (I) (wherein R is a hydrogen atom, a methyl group or a hydroxyl group) or a pharmacologically acceptable salt thereof.

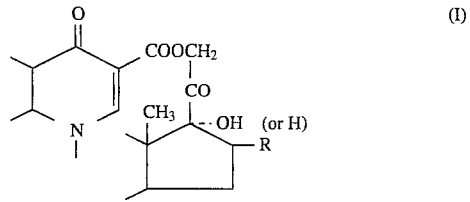

The compound of this invention has high antibacterial activity and antiinflammatory activity.

10 Claims, 2 Drawing Sheets

STEROID DERIVATIVES

BACKGROUND OF THE INVENTION

1. Field of the Invention

This invention rebates to a novel and useful ester compound having the structure of an ester between a quinolonecarboxylic acid and a steroid compound, a method for its production, and the use of the compound. More particularly, this invention relates to a compound having the structure of an ester between the carboxyl group of a quinolonecarboxylic acid and the alcoholic hydroxyl group in 21-position of asteroid compound or a pharmacologically acceptable salt thereof, to a method for the production of said compound and salt, and to an antibacterial composition and an antiinflammatory composition each comprising said compound or salt as an active ingredient.

2. Description of the Prior Art

In bacterial infections, the first therapeutic aim is to exterminate the bacteria with an antibiotic or antibacterial agent. While the antibiotics heretofore available are only sparingly active against MRSA (meticillin-resistant *Staphylococcus aureus*), synthetic antibacterial agents, typically quinolonecarboxylic acid, are considered promising and under intensive research. Meanwhile, bacterial infections are accompanied by inflammations in many clinical cases and, therefore, the concomitant administration of either a nonsteroidal or a steroidal antiinflammatory agent is a routine practice today. Of these antiinflammatory drugs, steroidal antiinflammatory agents have the disadvantage that although their antiinflammatory activity is high, they are prone to cause immunosuppression as a typical side effect and consequently increased susceptibility to bacterial infection. In any event, the administration of steroidal antiinflammatory agents call for the utmost caution against the risk of bacterial infection.

Under the circumstances the inventors of this invention conducted research on new compounds having both antibacterial and antiinflammatory actions which, if discovered, might solve the above-mentioned problems. In due course, the inventors of this invention succeeded in synthesizing a compound having the structure of an ester between the carboxyl group of a quinolonecarboxylic acid, which is a synthetic antibacterial agent, and the alcoholic hydroxyl group in 21-position of a steroid compound and a pharmacologically acceptable salt thereof and discovered that these compounds meet the above requirements. The findings were followed by further research, which has resulted in the development of this invention.

SUMMARY OF THE INVENTION

This invention relates to a compound having the structure of an ester between the carboxyl group of a quinolonecarboxylic acid and the alcoholic hydroxyl group in the 21-position of a steroid compound, which has the following formula (I) or a pharmacologically acceptable salt thereof (hereinafter referred to collectively as the present compound), to a method for the production of said compound and salt, and to an antibacterial composition and an antiinflammatory composition each comprising said compound or salt as an active ingredient.

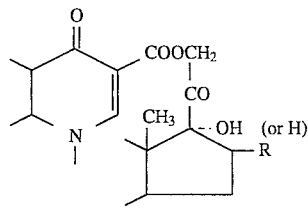

[wherein R is a hydrogen atom, a methyl group or a hydroxyl group]

DETAILED DESCRIPTION OF THE INVENTION

Figure 1:
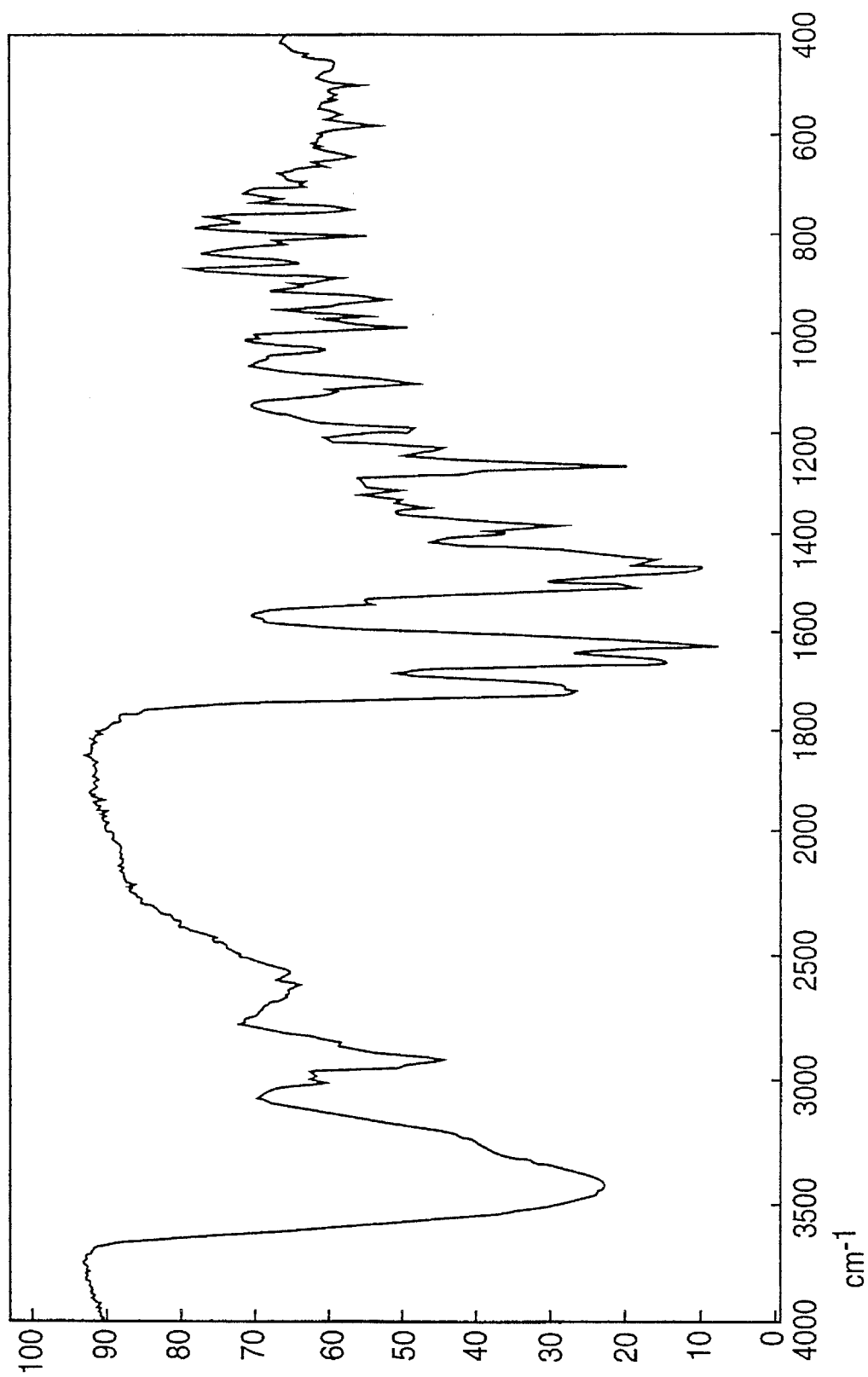
FIG. 1 is an infrared absorption spectrum (IR) of the compound synthesized in Example 1.
Figure 2:
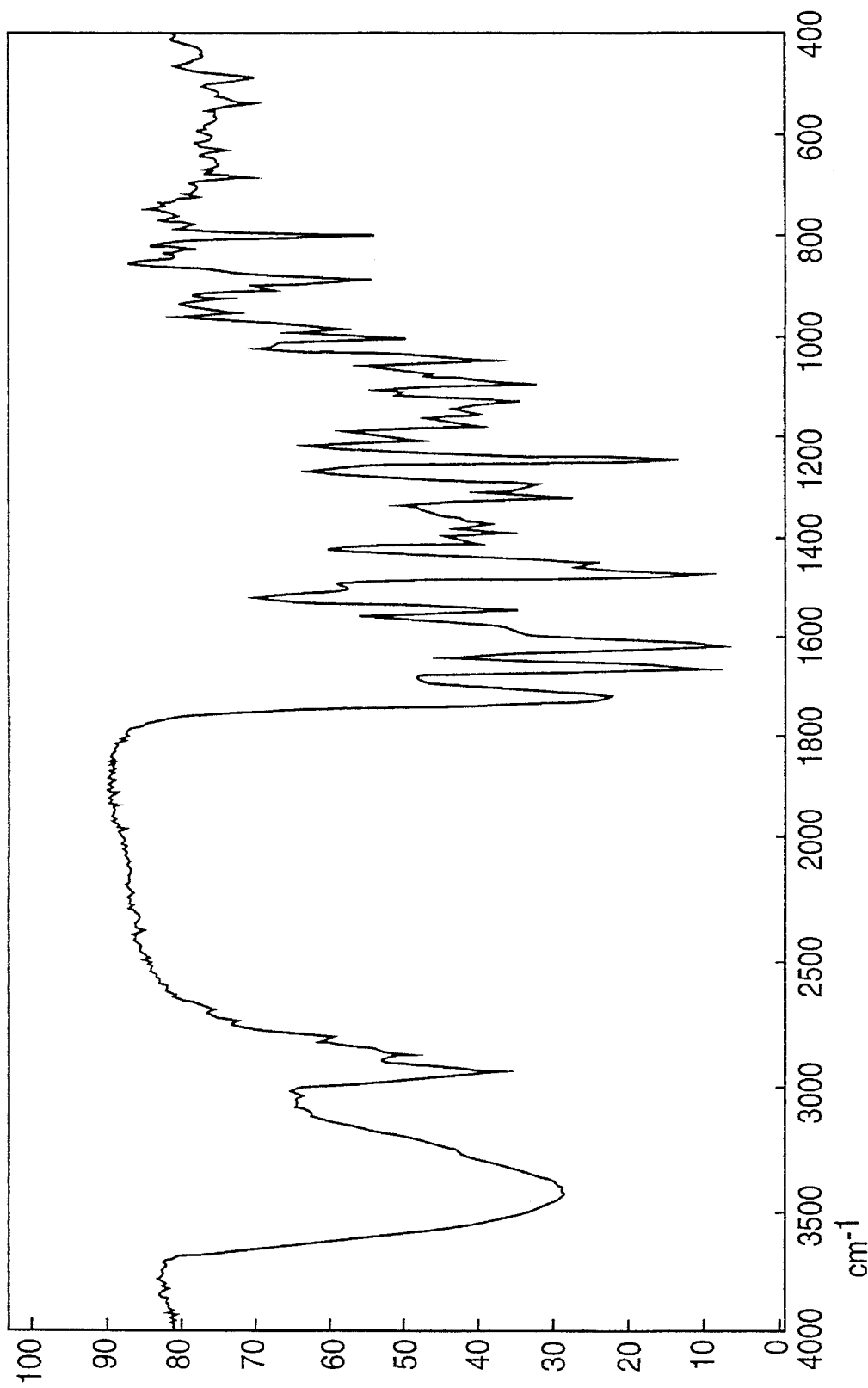
FIG. 2 is an infrared absorption spectrum (IR) of the compound synthesized in Example 6.

The steroid compound, which is a structural unit of the present compound, is any of the adrenocortical hormones (corticoids) secreted from the adrenal cortex. While these hormones are roughly classified into mineral corticoids and glucocorticoids according to differences in physiological activity, whichever of these types of corticoids can be employed for the purposes of this invention. In addition, any synthetic steroid having an alcoholic hydroxyl group or a halogen atom in the 21-position can be utilized in this invention.

The mineral corticoid which can be used as a structural unit of the present compound includes aldosterone, desoxycorticosterone, corticosterone and so on. Mineral corticoids are hormones having mineral-metabolizing activity and as such are associated with the metabolism of inorganic salts. Mineral corticoids modulate the excretion of sodium chloride and water, and being retained in the interstitium, promote the renal excretion of potassium and phosphate ions, thus being factors vital to animals for the maintenance of life.

The glucocorticoid that can be used as a structural unit of the present compound includes cortisone, hydrocortisone, triamcinolone acetonide, prednisolone, methylprednisolone, triamcinolone, dexamethasone, paramethasone, clocortolone, fluocinolone, and betamethasone. Glucocorticoids are corticosteroids having carbohydrate-metabolizing activity. Thus, they convert the body protein to carbohydrates and increase hepatic glycogen stores to increase the resistance of the body to shock, cold, trauma and poisoning.

The quinolonecarboxylic acid which can be used as the other structural unit of the present compound includes but is not limited to norfloxacin, ofloxacin, ciprofloxacin, lomefloxacin, fleroxacin and tosufloxacin. For example, 1-cyclopropyl-6,8-difluoro-1,4-dlhydro-4-oxo-7-[4-(4-aminobenzenesulfonyl)-1-piperazinyl]-3-quinolinecarboxylic acid which was synthesized for the first time by the inventors of this invention can also be used for the purposes of this invention.

More particularly, the compound of the invention may have the following formula or be a pharmacologically acceptable salt thereof:

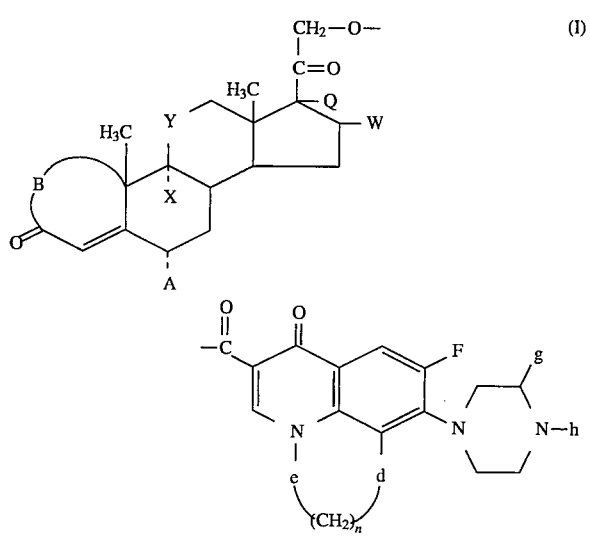

wherein the steroid moiety of the formula is a moiety selected from the group consisting of the following:

(1) A=X=W=H, B=—CH$_2$—CH$_2$—, Y=>C=O, Q=OH (cortisone);
(2) A=X=W=H, B=—CH$_2$—CH$_2$—, Y=>CH—OH, Q=OH (hydrocortisone);
(3) A=H, B=—CH=CH—, X=F, Y=>CH—OH, Q=W=acetal with acetone (triamcinolone acetonide);
(4) A=X=W=H, B=—CH=CH—, Y=>CH—OH, Q=OH (prednisolone);
(5) A=CH$_3$, B=—CH=CH—, X=W=H, Y=>CH—OH, Q=OH (methylprednisolone);
(6) A=H, B=—CH=CH—, X=F, Y=>CH—OH, Q=W=OH (triamcinolone);
(7) A=H, B=—CH=CH—, X=F, Y=>CH—OH, Q=OH, W=CH$_3$ (dexamethasone);
(8) A=F, B=—CH=CH—, X=H, Y=>CH—OH, Q=OH, W=CH$_3$ (paramethasone);
(9) A=F, B=—CH=CH—, X=Cl, Y=>CH—OH, W=CH$_3$, Q=H (clocortolone);
(10) A=X=F, B=—CH=CH—, Y=>CH—OH, Q=W=OH (fluocinolone);
(11) A=H, B=—CH=CH—, X=F, Y=>CH—OH, Q=OH, W=CH$_3$ (betamethasone);

and the quinolonecarboxylic acid moiety of the formula is a moiety selected from the group consisting of the following:

(12) n=0, d=g=h=H, e=C$_2$H$_5$ (norfloxacin);
(13) n=1, d=0, e=CHCH$_3$, g=H, h=CH$_3$ (ofloxacin);
(14) n=0, d=g=h=H, e=cyclopropyl (ciprofloxacin);
(15) n=0, d=F, e=C$_2$H$_5$, g=CH$_3$, h=H (lomefloxacin);
(16) n=0, d=F, e=CH$_2$CH$_2$F, g=H, h=CH$_3$ (fleroxacin);
(17) n=0, d=F, e=cyclopropyl, g=H, h=p-aminobenzensulfonyl (Ex. 5).

The present compound can be used, regardless of whether it is a free compound or a pharmacologically acceptable salt, for the purposes of this invention. The pharmacologically acceptable salt typically includes inorganic salts such as hydrochloride, sulfate and nitrate and organic salts such as acetate, maleate and tartrate. Aside from them, any other kind of salt can be used that is pharmacologically acceptable.

The present compound can be synthesized by the following two alternative processes or any improved or analogous processes.

The reaction schema for the production of the present compound through the reaction between a quinolonecarboxylic acid (II) and a steroid-21-halide (III) is first described. In the following formulas, X represents a halogen atom and R has the same meaning as defined hereinbefore.

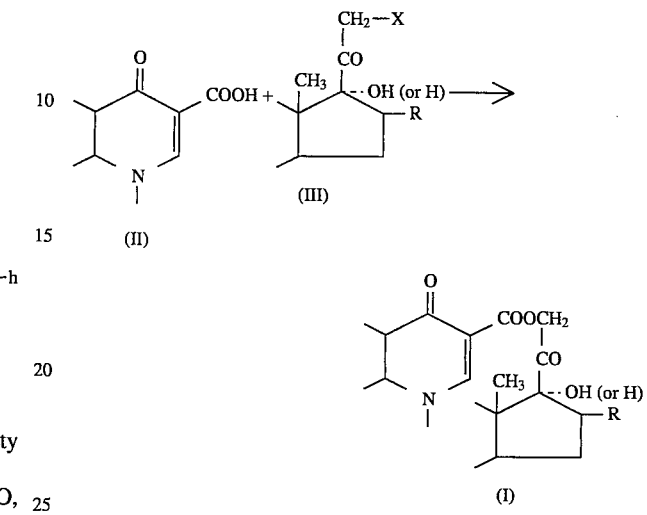

The present compound (I) can be obtained by reacting the quinolonecarboxylic acid (II) and steroid-21-halide (III) in an equimolar ratio in a solvent, such as acetone, methyl ethyl ketone, in the presence of a base (acid acceptor) at the reflux temperature. The reaction solvent is not limited to those mentioned but may be any solvent that does not interfere with the reaction. This reaction goes to completion in about 1 to 24 hours. The base (acid acceptor) for use in this reaction is preferably an organic amine such as pyridine or triethylamine. The halogen atom in 21-position of the steroid compound may for example be chlorine, bromine or iodine and the halogenation of the 21-position of the steroid compound can be carried out by any of the known methods (Journal of the Pharmaceutical Society of Japan, 81, 373, (1961)). The present compound (I) thus produced can be purified by recrystallization from a suitable solvent, for example a mixture of water with alcohol or acetone, dimethylformamide (DMF), alcohol, ethyl acetate, or a mixture of such solvents. Where necessary, the compound (I) may be further treated with an inorganic acid, e.g. hydrochloric acid, sulfuric acid, nitric acid, etc., or an organic acid, e.g. acetic acid, maleic acid, tartaric acid, etc., to provide the corresponding salt.

Now, the reaction schema for the production of the present compound (I) from the quinolonecarboxylic acid (II) and the steroid compound (VI) having an alcoholic hydroxyl group in 21-position by the mixed acid anhydride method is described below. In the formulas (IV) and (V), R$_1$ represents an alkyl group. In the formula (VI), R has the same meaning as defined -continued

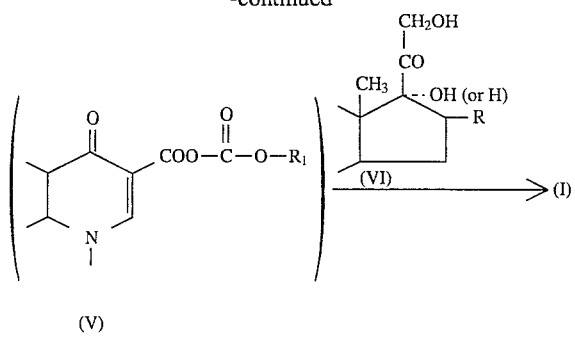

The present compound (I) can be obtained by preparing a mixed acid anhydride (V) of quinolonecarboxylic acid and reacting this anhydride with the steroid compound (VI) having an alcoholic hydroxyl group in 21-position. More specifically, the mixed acid anhydride (V) of quinolonecarboxylic acid is prepared by reacting the quinolonecarboxylic acid (II) with, for example, an alkyl chlorocarbonate (IV) (typically ethyl chlorocarbonate or butyl chlorocarbonate) in a solvent, such as chloroform or tetrahydrofuran (THF), in the presence of a base. The solvent that can be used in the step of preparing the mixed acid anhydride is not limited to those mentioned but may be any solvent that does not interfere with the reaction. This reaction goes to completion in about 1 to 15 minutes at about −5° C. to 0° C. The base for use in this reaction is preferably an organic amine such as triethylamine, tributylamine, etc. Then, the mixed acid anhydride (V) of quinolonecarboxylic acid thus obtained is reacted with the steroid compound (VI) having an alcoholic hydroxyl group in 21-position to provide the present compound (I) as an esterification product. The solvent that can be used for this esterification reaction is not limited to those mentioned but may be any solvent that does not interfere with the reaction. This reaction goes to completion when it is conducted at or below about 0° C. for about 30 minutes and, then, at room temperature for about 1 hour. The compound (I) thus obtained can be purified and, where necessary, converted to a salt in the same manner as described above.

The present compound (I) is a novel compound never heretofore described in the literature. Since it has both antibacterial and antiinflammatory activities, the present compound is a very useful compound capable of producing both antibacterial and antiinflammatory effects in monotherapy.

The inflammatory disease which can be treated with the antiinflammatory composition of this invention includes hemorrhoids, rheumatoid arthritis, degenerative rheumatism, spondylitis deformans, osteoarthritis, lumbago, gouty attack, pleurisy, acute otitis media, cystitis, prostatitis, toothache, uveitis, sinuitis and so on.

The antibacterial composition of this invention can be indicated with advantage in various bacterial infections caused by gram-negative and gram-positive bacteria.

The pharmaceutical composition of this invention can be administered either orally or otherwise as an antibacterial and antiinflammatory agent. The dosage form in which the composition of this invention can be supplied includes a variety of solid forms such as tablets, granules, powders, capsules, ointments, suppositories, etc. and liquid forms such as eyedrops, injections, syrups and so on. These dosage forms can be manufactured by the established pharmaceutical procedures. In the manufacture of such dosage forms, the known carriers and additives such as the excipient, binder, disintegrating agent, thickener, dispersant, reabsorption promoter, buffer, surfactant, preservative, isotonizing agent, stabilizing agent and pH control agent can be employed in appropriate amounts.

The pharmaceutical composition of this invention may contain one or more species of the present compound according to the intended use and need.

In application of the present compound as an antibacterial and antiinflammatory agent, its dosage depends on the species of compound, the type of disease, the patient's body weight and age, symptoms that must be treated, and the treatment regimen but the recommended daily dose for an adult is about 0.1 mg to about 30 mg in the case of an injectable preparation. In the case of an oral preparation, about 1 mg to about 100 mg can be administered a few times a day to the average adult. In the case of an ointment, a formulation containing about 0.01 to about 1% (w/w), preferably about 0.05 to about 0.5% (w/w), of the present compound can be applied to the affected area once to several times daily.

Unless contrary to the spirit and object of this invention, the pharmaceutical composition of this invention may further contain other antibacterial agents, inflammatory agents and/or other kinds of medicinal substances.

EXAMPLES

The following examples are further illustrative of this invention.

EXAMPLE 1

Process for Production of Norfloxacin-hydrocortisone Ester Hydrochloride

11β,17,21-Trihydroxy-4-pregnene-3,20-dione-21-[1-ethyl-6-fluoro-1,4-dihydro-7-(1-piperazinyl)-4-oxo-3-quinolinecarboxylate]hydrochloride To a mixture of 1.0 g of hydrocortisone-21-iodide and 0.68 g of norfloxacin is added 40 ml of acetone, followed by addition of 1 ml of triethylamine, and the mixture is refluxed for 3 hours. With the process of reaction, the norfloxacin dissolves gradually. After cooling, the precipitated crystals are collected by filtration and suspended in a mixture of ethanol and water. This suspension is made weakly basic using a 3% aqueous solution of sodium hydrogen carbonate for dissolution and the resulting solution is made acidic with hydrochloric acid, which causes separation of white crystals. This precipitate is collected by filtration and recrystallized from ethanol-water to provide 0.75 g of the title compound. m.p. 218°–220° C. (decomp.)

Elemental analysis for $C_{37}H_{46}FN_3O_7 \cdot HCl \cdot 3/2H_2O$. Calcd. (%): C, 61.11; H, 6.93; N, 5.78. Found (%) C, 61.17; H, 7.14; N 5.74

EXAMPLE 2

Process for Production of Norfloxacin-dexamethasone Ester Hydrochloride

9-Fluoro-11β,17,21-trihydroxy-16α-methyl-1,4-pregnadiene-3,
20-dione-21-[1-ethyl-6-fluoro-1,4-dihydro-7-(1-piperazinyl)-4-oxo-3-quinolinecarboxylate]-hydrochloride Using 0.79 g of dexamethasone-21-iodide, 0.5 g of norfloxacin, 1 ml of triethylamine and 40 ml of acetone, the reaction is carried out in otherwise the same manner as Example 1. After removal of the solvent, the precipitated crystals are collected by filtration and rinsed. This crystalline hydroiodide is converted to the hydrochloride in the same manner as Example 1. The crystal crop thus obtained is recrystallized from ethanol to provide 0.55 g of the title compound. m.p. 214°–216° C. (decomp.)

Elemental analysis for $C_{38}H_{45}F_2N_3O_7 \cdot HCl \cdot 3/2H_2O$. Calcd. (%): C, 60.27; H, 6.52; N, 5.55. Found (%): C, 60.56; H, 6.76; N, 5.23.

EXAMPLE 3

Process for Production of Norfloxacin-cortisone Ester Hydrochloride 17,21-Dihydroxy-4-pregnene-3,11,20-trione-21-[1-ethyl-6-fluoro-1,4-dihydro-7-(1-piperazinyl)-4-oxo-3-quinolinecarboxylate]hydrochloride Using 1.0 g of cortisone-21-iodide, 0.6 g of norfloxacin, 2 ml of triethylamine, 10 ml of acetone and 10 ml of DMF, the reaction is conducted in the same manner as Example 1. After removal of the solvent, water is added and the precipitated crystals are collected by filtration. This crystalline hydroiodide is converted to the hydrochloride in the same manner as Example 1. This product is recrystallized from DMF-ethyl acetate to provide 0.3 g of the title compound as white crystals. m.p. 202°–204° C. (decomp.)

Elemental analysis for $C_{37}H_{44}FN_3O_7 \cdot HCl \cdot 3/4H_2O$. Calcd. (%): C, 62.44; H, 6.59; N, 5.90. Found (%): C, 62.42; H, 6.41; N, 5.69.

EXAMPLE 4

Process for Production of Lomefloxacin-hydrocortisone Ester Hydrochloride

11β,17,21-Trihydroxy-4-pregnene-3,20-dione-21-[(±)-1-ethyl-6,8-difluoro-1,4-dihydro-7-(3-methyl-1-piperazinyl)-4-oxo-3-quinolinecarboxylate]-hydrochloride Using 0.47 g of hydrocortisone-21-iodide, 0.39 g of lomefloxacin, 3 ml of triethylamine, 50 ml of acetone and 10 ml of DMF, the reaction is conducted in otherwise the same manner as Example 1. After removal of the solvent, water is added and the precipitated crystals are collected by filtration. This hydroiodide is converted to the hydrochloride in the same manner as Example 1. This product is recrystallized from ethanol-water to provide 0.15 g of the title compound. m.p. 218°–220° C. (decomp.)

Elemental analysis for $C_{38}H_{47}F_2N_3O_7 \cdot HCl \cdot 2H_2O$. Calcd. (%): C, 59.41; H, 6.82; N, 5.47. Found (%): C, 59.35; H, 6.92; N, 5.51.

EXAMPLE 5

Process for Production of 9-fluoro-11β,17,21-trihydroxy-16α-methyl-1,4-pregnadiene-3,20-dione-21-[1-cyclopropyl-6,8-difluoro-7-[4-(4-aminobenzenesulfonyl)-1-piperazinyl]-1,4-dihydro-4-oxo-3-quinolinecarboxylate]

In 100 ml of pyridine is suspended 1.85 g of 1-cyclopropyl-6,8-difluoro-1,4-dihydro-4-oxo-7-(1-piperazinyl)-3-quinolinecarboxylic acid, under stirring and ice-cooling, 20 ml of a solution prepared by dissolving 4.95 g of acetamidobenzenesulfonyl chloride in benzene is gradually added. The mixture is stirred under ice-cooling for 1 hour and, then, at room temperature for 3 hours. The reaction mixture is then concentrated under reduced pressure and the residue is dissolved in 1N-aqueous sodium hydroxide solution. This solution is adjusted to pH 4 with acetic acid and the precipitated crystals are recovered by filtration. The crystals are rinsed and recrystallized from DMF-ethanol to provide 2.71 g of 1-cyclopropyl-6,8-difluoro-1,4-dihydro-4-oxo-7-[4-(4-acetamidobenzenesulfonyl)-1-piperazinyl]-3quinolonecarboxylic acid. m.p. 288°–290° C. (decomp.)

The compound thus obtained, 2.15 g, is refluxed in a mixture of 100 ml of 2N-hydrochloric acid and 50 ml of ethanol with stirring for 2 hours. The reaction mixture is then concentrated under reduced pressure and the residue is dissolved in 1N-aqueous sodium hydroxide solution. The solution is adjusted to pH 7.0 with acetic acid and the precipitated crystals are collected by filtration and rinsed. This crop of crystals is dissolved in water and adjusted to pH 4 with acetic acid and any insoluble fraction is filtered off. The filtrate is adjusted to pH 7.0 with 2N-sodium hydroxide solution and the precipitated crystals are collected by filtration and rinsed. This crop is crystallized from dimethylformamide-ethanol to provide 2.15 g of 1-cyclopropyl-6,8-difluoro-1,4-dihydro-4-oxo-7-[4-(4-aminobenzenesulfonyl)-1-piperazinyl]-3-quinolinecarboxylic acid (*). m.p. 280°–282° C. (decomp.)

Elemental analysis for $C_{23}H_{22}F_2N_4O_5S \cdot 1/4H_2O$. Calcd. (4): C, 54.27 H, 4.46; N, 11.01. Found (4): C, 54.29 H, 4.46; N. 11.02.

(*) This compound is a novel quinolonecarboxylic acid synthesized for the first time by the inventors of this invention.

A mixture of 0.76 g of dexamethasone-21-iodide, 0.75 g of 1-cyclopropyl-6,8-difluoro-7-[4-(4-aminobenzenesulfonyl)-1-piperazinyl]-1,4-dihydro-4-oxo-3-quinolinecarboxylic acid as prepared by the above process, 1 ml of triethylamine, 50 ml of acetone and 5 ml of DMF is refluxed in the same manner as Example 1 for 8 hours. The solvent is then distilled off under reduced pressure and the precipitated crystals are collected by filtration and rinsed. The crystals are dissolved in chloroform and washed serially with 3% aqueous sodium hydrogen carbonate solution and water and the solvent is distilled off. The crystalline residue is recrystallized from acetone-water to provide 0.50 g of the title compound. m.p. 198°–200° C. (decomp.)

Elemental analysis for $C_{45}H_{49}F_3N_4O_9S \cdot 1/2H_2O$. Calcd. (4): C, 60.87; H, 5.68; N, 6.31. Found (%): C, 60.59; H, 5.62; N, 6.22.

EXAMPLE 6

Process for Production of Ofloxacin-dexamethasone Ester

9-Fluoro-11β,17,21-trihydroxy-16α-methyl-1,4-pregnadiene-3,20-dione-21-[(±)-9-fluoro-2,3-dihydro-3-methyl-10-(4-methyl-1-piperazinyl)-7-oxo-7H-pyrido[1,2,3-de][1,4]benzoxazine-6-carboxylate]

In 30 ml of chloroform is dissolved 0.57 g of ofloxacin followed by addition of 0.4 ml of triethylamine. The solution is cooled to a temperature not over 0° C. Then, 0.2 ml of ethyl chlorocarbonate is slowly added portionwise and the mixture is stirred for 5 minutes. Then, a solution of 0.62 g of dexamethasone in pyridine is added dropwise. The mixture is further stirred under cooling for 30 minutes and, then, at room temperature for 1 hour. The solvent is then distilled off and water is added to the residue. The precipitated crystals are collected by filtration and recrystallized from dimethylformamide-isopropyl ether to provide 0.15 g of the title compound as white crystals. m.p. 191°–193° C. (decomp.)

Elemental analysis for $C_{40}H_{47}F_2N_3O_8 \cdot H_2O$. Calcd. (%): C, 63.73; H, 6.55; N, 5.57. Found (%): C, 63.69; H, 6.42; N, 5.46.

EXAMPLE 7

Process for Production of Ofloxacin-triamcinolone Acetonide Ester

9-Fluoro-11β,21-dihydroxy-16α,17-isopropylidene-dioxy-1,4-pregnadiene-3,20-dione-21-[(±)-9-fluoro-2,3-dihydro-3-methyl-10-(4-methyl-1-piperazinyl)-7-oxo-7H-pyrido[1,2,3-de][1,4]benzoxazine-6-carboxylate]

Using 0.42 g of ofloxacin, 30 ml of chloroform, 0.3 ml of triethylamine and 0.5 g of triamcinolone acetonide, the reaction and workup procedure of Example 6 is otherwise repeated. The resulting crystals are recrystallized from dimethylformamide-isopropyl ether to provide 0.16 g of the title compound as white crystals. m.p. 206°–208° C. (decomp.)

Elemental analysis for $C_{42}H_{49}F_2N_3O_9 \cdot 3/2H_2O$. Calcd. (%): C, 62.67; H, 6.51; N, 5.22. Found (%): C, 62.49; H, 6.33; N, 5.03.

EXAMPLE 8

Inhibitory Effect of the Compound on Rat Carrageenin-induced Pleuritis

The inhibitory effect of norfloxacin-dexamethasone ester hydrochloride on rat carrageenin-induced pleuritis was evaluated.

[Test substance] Norfloxacin-dexamethasone ester hydrochloride (abbreviated name: NFLX-DX)

[Test Method]

Wistar rats weighing about 200 g were used. Two groups receiving (1) distilled water (5 ml/kg) and (2) NFLX-DX (13.4 mg/kg), respectively, were provided. Under pentobarbital anesthesia, 0.1 ml of 2% λ-carrageenin was injected into the rat pleura to induce pleuritis. Five hours after the construction of pleuritis, a 5% aqueous solution of Pontamine Sky Blue (2 mg/kg) was injected intravenously, and 20 minutes later the rat was sacrificed and the pleural exudate was collected using a tube. The amount of dye leakage in the pleural cavity (μg/site) was estimated from the amount and absorbance (625 nm) of the exudate sample (ml) by the calibration curve method. The test substance was administered orally (5 ml/kg) 30 minutes before induction of inflammation.

[Test results]
The results are shown in table 1.

TABLE 1

The effect of the compound on rat carrageenin-induced pleuritis

| group | n | Dye leakage (μ g/site) | % Inhibition |
|---|---|---|---|
| Control (distilled water) | 8 | 74.81 ± 10.70 | — |
| NFLX-DX | 7 | 20.02 ± 3.80* | 73.0 |

The value of dye leakage represents the mean ± standard error.
*Significant difference from the control group, p < 0.01.

It is apparent from Table 1 that the present compound significantly inhibited rat carrageenin-induced pleuritis.

FORMULATION EXAMPLE 1

| Oral tablet | |
|---|---|
| Compound of Example 2 | 100 mg |
| Lactose | 80 mg |
| Starch | 17 mg |
| Magnesium stearate | 3 mg |

Using the above ingredients per tablet, tablets are manufactured by the routine procedures. If necessary, the tablets ;,may be sugar-coated.

FORMULATION EXAMPLE 2

| Eyedrops | |
|---|---|
| Compound of Example 6 | 200 mg |
| Boric acid | 700 mg |
| Borax | 300 mg |
| Sodium chloride | 500 mg |
| Polyvinyl alcohol | 100 mg |
| Benzalkonium chloride | 5 mg |
| Sterile purified water | to make 100 ml |

The above ingredients are mixed in the routine manner to provide eyedrops.

FORMULATION EXAMPLE 3

| Ointment | |
|---|---|
| Compound of Example 7 | 100 mg |
| Hydrophilic ointment base | to make 100 g |

The above ingredients are mixed in the routine manner to provide an ointment.

The novel steroid derivative of this invention has both antibacterial and antiinflammatory activities and is a very useful compound capable of producing the effect of an antibacterial agent and that of an antiinflammatory agent in monotherapy.

What is claimed is:

1. A compound having the structure of an ester between the carboxyl group of a quinolonecarboxylic acid and the alcoholic hydroxyl group in 21-position of a steroid compound, which has the following formula (I) or a pharmacologically acceptable salt thereof

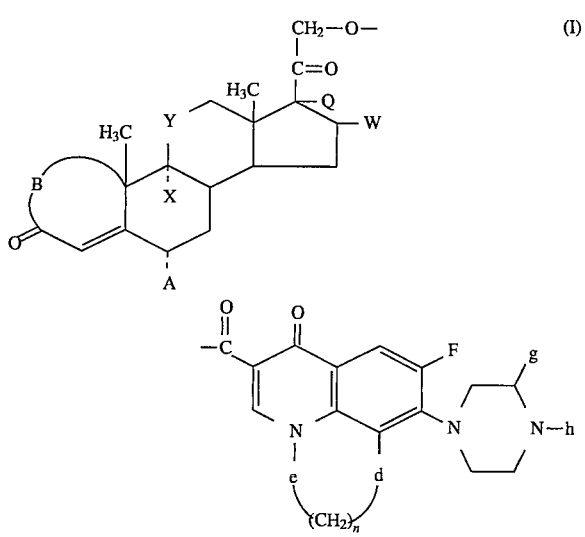

wherein the steroid moiety of the formula is a moiety selected from the group consisting of the following:

(1) A=X=W=H, B=—CH₂—CH₂—, Y=>C=O, Q=OH (cortisone);
(2) A=X=W=H, B=—CH₂—CH₂—, Y=>CH—OH, Q=OH (hydrocortisone);
(3) A=H, B=—CH=CH—, X=F, Y=>CH—OH, Q=W=acetal with acetone (triamcinolone acetonide);
(4) A=X=W=H, B=—CH=CH—, Y=>CH—OH, Q=OH (prednisolone);
(5) A=CH₃, B=—CH=CH—, X=W=H, Y=>CH—OH, Q=OH (methylprednisolone);
(6) A=H, B=—CH=CH—, X=F, Y=>CH—OH, Q=W=OH (triamcinolone);
(7) A=H, B=—CH=CH—, X=F, Y=>CH—OH, Q=OH, W=CH₃ (dexamethasone);
(8) A=F, B=—CH=CH—, X=H, Y=>CH—OH, Q=OH, W=CH₃ (paramethasone);
(9) A=F, B=—CH=CH—, X=Cl, Y=>CH—OH, W=CH₃, Q=H (clocortolone);
(10) A=X=F, B=—CH=CH—, Y=>CH—OH, Q=W=OH (fluocinolone);
(11) A=H, B=—CH=CH—, X=F, Y=>CH—OH, Q=OH, W=CH₃ (betamethasone);

and the quinolonecarboxylic acid moiety of the formula is a moiety selected from the group consisting of the following:

(12) n=0, d=g=h=H, e=C₂H₅ (norfloxacin);
(13) n=1, d=0, e=CHCH₃, g=H, h=CH₃ (ofloxacin);
(14) n=0, d=g=h=H, e=cyclopropyl (ciprofloxacin);
(15) n=0, d=F, e=C₂H₅, g=CH₃, h=H (lomefloxacin);
(16) n=0, d=F, e=CH₂CH₂F, g=H, h=CH₃ (fleroxacin);
(17) n=0, d=F, e=cyclopropyl, g=H, h=p-aminobenzensulfonyl.

2. The compound of claim 1 which is 11β,17,21-trihydroxy-4-pregnene-3,20-dione-21-[1-ethyl-6-fluoro-1,4-dihydro-7-(1-piperazinyl)-4-oxo-3-quinolinecarboxylate] or a pharmacologically acceptable salt thereof.

3. The compound of claim 1 which is 9-fluoro-11β,17,21-trihydroxy-16α-methyl-1,4-pregnadiene-3,20-dione-21-[1-ethyl-6-fluoro-1,4-dihydro-7-(1-piperazinyl)-4-oxo-3-quinolinecarboxylate] or a pharmacologically acceptable salt thereof.

4. The compound of claim 1 which is 17,21-dihydroxy-4-pregnene-3,11,20-trione-21-[1-ethyl-6-fluoro-1,4-dihydro-7-(1piperazinyl)-4-oxo-3-quinolinecarboxylate] or a pharmacologically acceptable salt thereof.

5. The compound of claim 1 which is 11β,17,21-trihydroxy-4-pregnene-3,20-dione-21-[(±)-1-ethyl-6,8-difluoro-1,4-dihydro-7-(3-methyl-1-piperazinyl)-4-oxo-3-quinolinecarboxylate] or a pharmacologically acceptable salt thereof.

6. The compound of claim 1 which is 9-fluoro-11β,17,21-trihydroxy-16α-methyl-1,4-pregnadiene-3,20-dione-21-[1-cyclopropyl-6,8-difluoro-7-[4-(4-aminobenzenesulfonyl)-1-piperazinyl]-1,4-dihydro-4-oxo-3-quinolinecarboxylate] or a pharmacologically acceptable salt thereof.

7. The compound of claim 1 which is 9-fluoro-11β,17,21-trihydroxy-16α-methyl-1,4-pregnadiene-3,20-dione-21-[(±)-9-fluoro-2,3-dihydro-3-methyl-10-(4-methyl-1-piperazinyl)-7-oxo-7H-pyrido[1,2,3-de][1,4]benzoxazine-6-carboxylate] or a pharmacologically acceptable salt thereof.

8. The compound of claim 1 which is 9-fluoro-11β,21-dihydroxy-16α,17-isopropylidenedioxy-1,4-pregnadiene-3,20-dione-21-[(±)-9-fluoro-2,3-dihydro-3-methyl-10-(4-methyl-1-piperazinyl)-7-oxo-7H-pyrido[1,2,3-de][1,4]benzoxazine-6-carboxylate] or a pharmacologically acceptable salt thereof.

9. An antibacterial composition comprising an antibacterial effective amount of the compound or pharmacologically acceptable salt thereof claimed in claim 1 as an active ingredient.

10. An antiinflammatory composition comprising an antiinflammatory effective amount of the compound or pharmacologically acceptable salt thereof claimed in claim 1 as an active ingredient.

* * * * *